United States Patent
Nakatsuji et al.

(10) Patent No.: US 10,352,843 B2
(45) Date of Patent: Jul. 16, 2019

(54) CELL ASSESSMENT METHOD, CELL ASSESSMENT DEVICE, AND CELL ASSESSMENT PROGRAM

(71) Applicants: Kyoto University, Kyoto-shi, Kyoto (JP); HAMAMATSU PHOTONICS K.K., Hamamatsu-shi, Shizuoka (JP)

(72) Inventors: Norio Nakatsuji, Kyoto (JP); Norikazu Sugiyama, Hamamatsu (JP); Yoshinori Mizuguchi, Hamamatsu (JP); Tadashi Fukami, Hamamatsu (JP); Hidenao Yamada, Hamamatsu (JP); Toyohiko Yamauchi, Hamamatsu (JP); Yumi Kakuno, Hamamatsu (JP)

(73) Assignees: KYOTO UNIVERSITY, Kyoto-shi (JP); HAMAMATSU PHOTONICS K.K., Hamamatsu-shi, Shizuoka (JP)

(*) Notice: Subject to any disclaimer, the term of this patent is extended or adjusted under 35 U.S.C. 154(b) by 67 days.

(21) Appl. No.: 15/037,142

(22) PCT Filed: Oct. 17, 2014

(86) PCT No.: PCT/JP2014/077727
§ 371 (c)(1),
(2) Date: May 17, 2016

(87) PCT Pub. No.: WO2015/076042
PCT Pub. Date: May 28, 2015

(65) Prior Publication Data
US 2016/0349170 A1  Dec. 1, 2016

(30) Foreign Application Priority Data
Nov. 19, 2013 (JP) .................................. 2013-238832

(51) Int. Cl.
*G06K 9/00* (2006.01)
*G01N 15/14* (2006.01)
(Continued)

(52) U.S. Cl.
CPC ......... *G01N 15/1434* (2013.01); *C12M 41/36* (2013.01); *G01N 15/1475* (2013.01);
(Continued)

(58) Field of Classification Search
USPC .................................................. 382/128–134
See application file for complete search history.

(56) References Cited

U.S. PATENT DOCUMENTS

| 2003/0108231 A1* | 6/2003 | Hamahashi | G06K 9/00127 |
| | | | 382/133 |
| 2008/0032325 A1* | 2/2008 | DiMarzio | G02B 21/0004 |
| | | | 435/29 |
| 2010/0284016 A1* | 11/2010 | Teitell | G01J 3/453 |
| | | | 356/451 |

FOREIGN PATENT DOCUMENTS

JP    2012-231709 A    11/2012

OTHER PUBLICATIONS

Norikazu Sugiyama et al., "Label-free characterization of living human induced pluripotent stem cells by subcellular topographic imaging technique using full-field quantitative phase microscopy coupled with interference reflection microscopy," (published online Aug. 22, 2012), Biomedical Optics Express, Sep. 1, 2012, pp. 2175-2183, vol. 3, No. 9.

(Continued)

Primary Examiner — Alex Kok S Liew
(74) Attorney, Agent, or Firm — Drinker Biddle & Reath LLP

(57) ABSTRACT

The present invention relates to a cell assessment method characterized in including an acquisition step of acquiring an
(Continued)

optical path length image of a small cell clump, an extraction step of extracting a cell nucleus region within the acquired optical path length image, a comparison step of comparing an optical path length of an inside and an optical path length of an outside of the extracted cell nucleus region, and an assessment step of assessing whether or not a cell is a stem cell based on the comparison results.

9 Claims, 13 Drawing Sheets

(51) Int. Cl.
  *G01N 33/50*   (2006.01)
  *C12M 1/34*   (2006.01)
  *G01N 15/10*   (2006.01)

(52) U.S. Cl.
  CPC ....... *G01N 33/5073* (2013.01); *G06K 9/0014* (2013.01); *G06K 9/00134* (2013.01); *G06K 9/00147* (2013.01); *G01N 2015/1006* (2013.01); *G01N 2015/144* (2013.01); *G01N 2015/1447* (2013.01)

(56) References Cited

OTHER PUBLICATIONS

International Preliminary Report on Patentability dated Jun. 2, 2016 for PCT/JP2014/077727.

\* cited by examiner

Fig.5
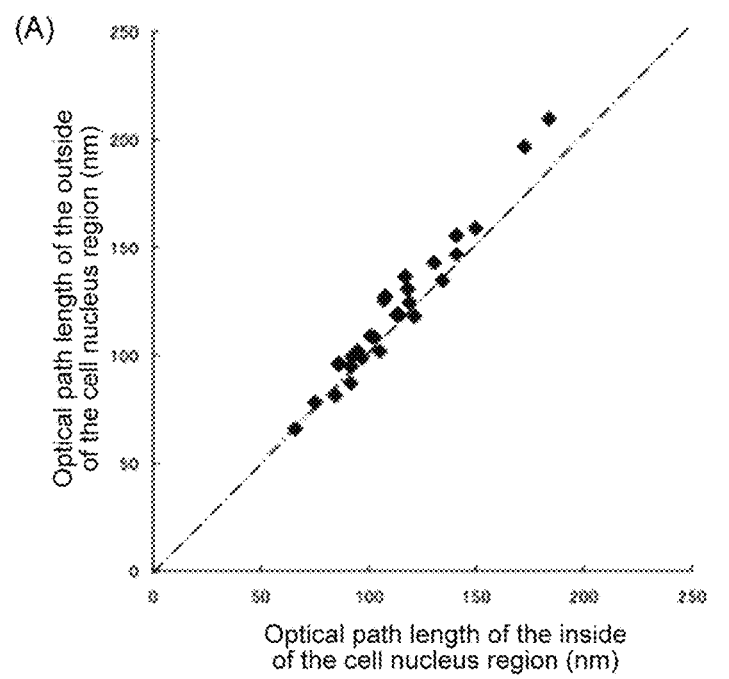
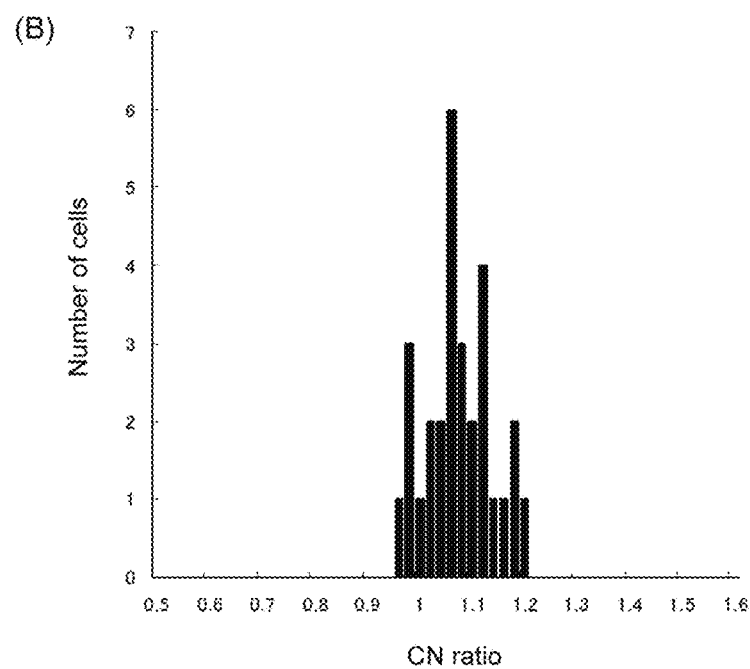

*Fig.7*
(A)
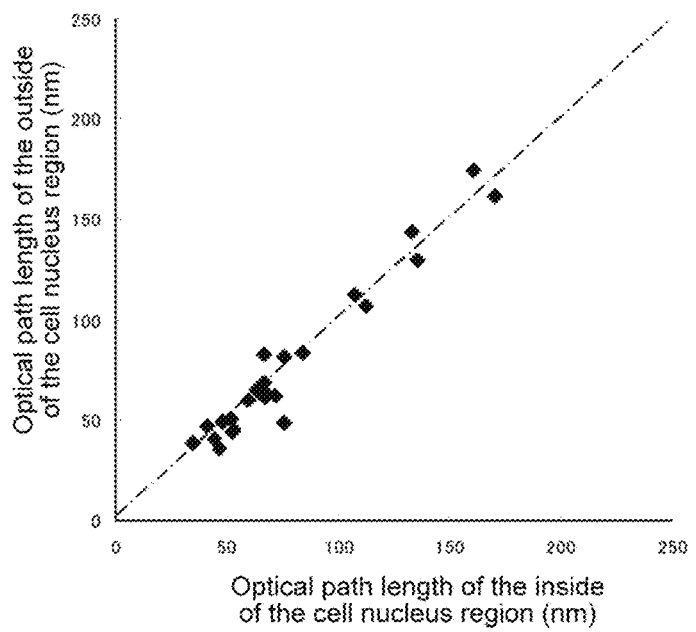
(B)
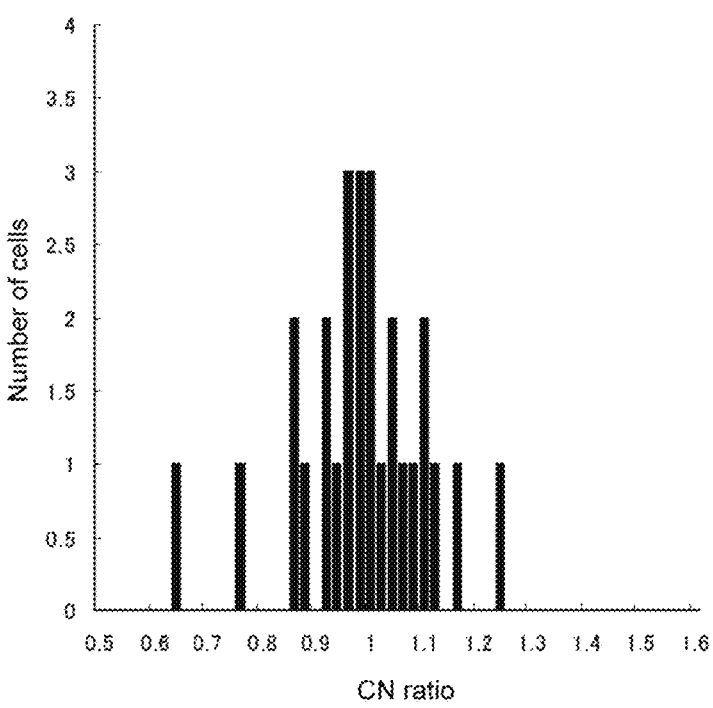

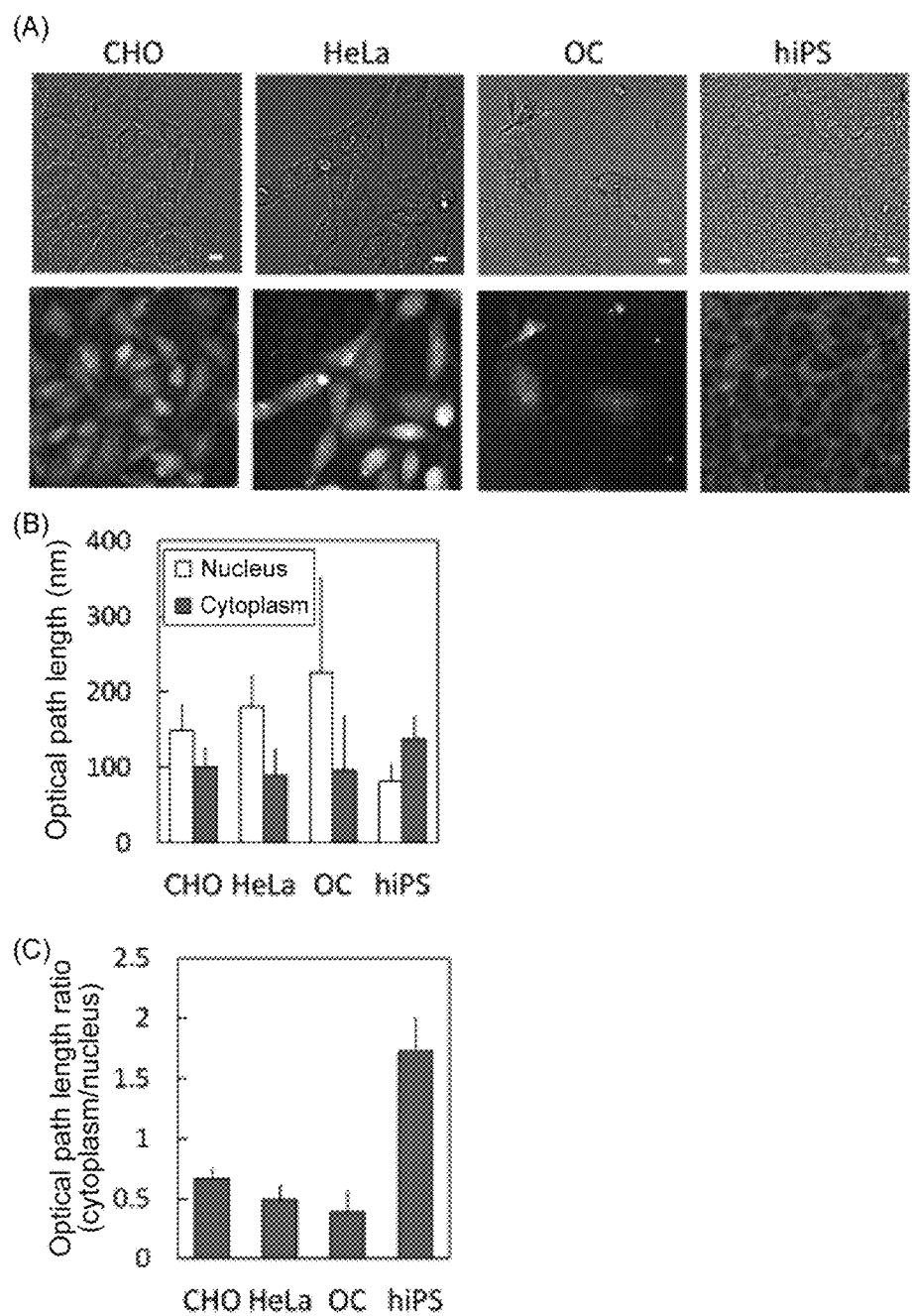

CELL ASSESSMENT METHOD, CELL ASSESSMENT DEVICE, AND CELL ASSESSMENT PROGRAM

TECHNICAL FIELD

The present invention relates to a cell assessment method, a cell assessment device, and a cell assessment program.

BACKGROUND ART

Human-derived stem cells such as ES cells and iPS cells have an ability to differentiate into many kinds of cells (pluripotency), and have attracted attention in that they enable large-scale pharmacometrics and medical applications using human cells which have been difficult, such as analysis of diseases, drug discovery screening, toxicity testing, and regenerative medicine. A differentiation efficiency in differentiation induction from these stem cells into desired cells is considered to be largely dependent on the state of the stem cells as starting materials. That is, the efficiency of differentiation induction is lowered, unless the stem cells maintain pluripotency and keep an undifferentiated state. Thus, quality control of the stem cells is extremely important for industrial application of the stem cells, and the stem cells need to be monitored and noninvasively assessed for their states.

In addition, since these stem cells form a confluent cell population (colony) by adhesion (contact) of approximately thousands to tens of thousands of stem cells, quality control is also usually conducted in increments of colonies.

For example, Patent Document 1 discloses a cell analytical method in a cell analyzer for analyzing a cell colony using an optical path length image of a cell colony composed of a large number of cells, which is characterized by comprising an obtention step of obtaining the optical path length image of the cell colony by an obtention means in the cell analyzer, an extraction step of extracting a circular shape corresponding to the cell nucleus of the cell in the obtained optical path length image by an extraction means in the cell analyzer, a comparison step of comparing an inner optical path length with an outer optical path length of the extracted circular shape by the comparison means of the cell analyzer, and an analysis step of analyzing the cell colony by an analysis means in the cell analyzer based on the compared results.

In addition, Non-Patent Document 1 describes that mean optical path lengths in cytoplasm regions in CHO cells, HeLa cells and osteoclast-like (OC) cells which were differentiated cells were smaller than those in their nuclear areas, on the contrary, a mean optical path length in cytoplasm region in each hiPS cell in the colony was larger than that in its nuclear area, and that a ratio (cytoplasm/nucleus) of optical path lengths can be a simple indicator for discriminating between the hiPS cells and other types of differentiated cells.

CITATION LIST

Patent Literature

Patent Document 1: Japanese Patent Application Laid-Open No. 2012-231709

Non Patent Literature

Non-Patent Document 1: Biomedical Optics Express, Vol. 3, issue 9, pp. 2175-2183 (2012).

SUMMARY OF INVENTION

Problems to be Solved by the Invention

According to Patent Document 1, an "optical path length" is a result of multiplying "refractive index" by "physical thickness" (optical path length =refractive index×physical thickness) and the refractive index of a cell nucleus (inside of the cell nucleus) is generally lower than the refractive index of cytoplasm (outside of the cell nucleus) (refractive index of the inside of the cell nucleus<refractive index of the outside of the cell nucleus).

Stem cells of good quality that form a colony have shapes such as shown in FIG. 12 with distances between adjacent stem cells being close and the cytoplasm being thick between cell nuclei so that the physical thicknesses at the inside and the outside of the cell nucleus are substantially equal (physical thickness of the inside of the cell nucleus≈physical thickness of the outside of the cell nucleus) and in regard to the optical path length, it is deemed that "optical path length of the inside of the cell nucleus<optical path length of the outside of the cell nucleus" holds.

On the other hand, with stem cells of poor quality that form a colony, the distances between adjacent stem cells are far and the cytoplasm between cell nuclei is thin so that physical thickness of the inside of the cell nucleus is much thicker than the physical thickness of the outside (physical thickness of the inside of the cell nucleus>>physical thickness of the outside of the cell nucleus) and in regard to the optical path length, it is deemed that "optical path length of the inside of the cell nucleus>optical path length of the outside of the cell nucleus" holds.

Thus in Patent Document 1, it is deemed that whether or not "optical path length of the inside of the cell nucleus<optical path length of the outside of the cell nucleus" holds depends on the physical thickness of the outside of the cell nucleus, and the physical thickness of the outside of the cell nucleus depends on the shape of the cell.

On the other hand, in order to maintain stem cells, it is essential to perform subculturing by dissociating a stem colony into small clumps and making these proliferate. Although in the process of subculturing, it is desirable to assess the quality of the dissociated small clump product obtained from the stem cell colony and then make these proliferate, the shapes of the stem cells forming the stem cell colony are not necessarily maintained in the process of dissociating the stem cell colony into small clumps because the adhesion (contact) of a stem cell with other cells is severed partially or completely. For example, FIG. 1 is an image acquired by observing, under a bright field microscope, a single ES cell that is a dissociated small clump product obtained from an ES cell colony (bright field image; a single ES cell region is provided with the symbol W), and in FIG. 1, the cell nucleus of the single ES cell is biased in position and the thickness of the cytoplasm is also non-uniform.

It was thus considered that for a stem cell forming a small cell clump, "optical path length of the inside of the cell nucleus<optical path length of the outside of the cell nucleus" does not hold.

On the other hand, although it was known that with differentiated cells, the average optical path length of cytoplasmic regions is less than the average optical path length of nucleus regions and that with respective hiPS cells in a colony, the average optical path length of cytoplasmic regions is greater than the average optical path length of nucleus regions (FIG. 13), it was predicted that when an hiPS cell colony is dissociated into small clumps, "optical path length of the inside of the cell nucleus<optical path length of the outside of the cell nucleus" will not hold.

However, the present inventors found that even for a stem cell forming a small cell clump, "optical path length of the inside of the cell nucleus<optical path length of the outside of the cell nucleus" holds regardless of shape and noticed that it is possible to assess whether or not a cell forming a small cell clump is a stem cell by comparing the optical path length of the inside of the cell nucleus region and the optical path length of the outside.

The present invention is based on this unexpected finding and an object thereof is to provide a cell assessment method, a cell assessment device, and a cell assessment program for assessing whether or not a cell forming a small cell clump is a stem cell.

Means for Solving the Problems

The present invention that achieves the above object is a cell assessment method characterized in including an acquisition step of acquiring an optical path length image of a small cell clump, an extraction step of extracting a cell nucleus region within the acquired optical path length image, a comparison step of comparing an optical path length of an inside and an optical path length of an outside of the extracted cell nucleus region, and an assessment step of assessing whether or not a cell is a stem cell based on the comparison results.

Also, the present invention is a cell assessment device characterized in including an acquisition means acquiring an optical path length image of a small cell clump, an extraction means extracting a cell nucleus region within the acquired optical path length image, a comparison means comparing an optical path length of an inside and an optical path length of an outside of the extracted cell nucleus region, and an assessment means assessing whether or not a cell is a stem cell based on the comparison results.

Further, the present invention is a program arranged to make a computer function as an acquisition means acquiring an optical path length image of a small cell clump, an extraction means extracting a cell nucleus region within the acquired optical path length image, a comparison means comparing an optical path length of an inside and an optical path length of an outside of the extracted cell nucleus region, and an assessment means assessing whether or not a cell is a stem cell based on the comparison results.

In the present invention, a "small cell clump" means a cell cluster that includes not more than 200 cells, and a "stem cell" means a cell having an ability to differentiate into cells of multiple lineages (pluripotency) and an ability to maintain the pluripotency even after undergoing cell division (replication competence).

Also, "optical path length" is synonymous with "phase difference" or "optical thickness" and is a result of multiplying "refractive index" by "physical thickness" (optical path length=refractive index×physical thickness). An "optical path length image" is an image from which an optical path length can be acquired.

For a stem cell forming a small cell clump, "optical path length of the inside of the cell nucleus region<optical path length of the outside of the cell nucleus region" holds regardless of shape and therefore, by the present invention, whether or not cells are stem cells can be assessed even with cells that form a small cell clump.

Also, if the small cell clump is a dissociated small clump product obtained from a colony of pluripotent stem cells, for example, iPS cells or ES cells, the dissociated small clump product may be selected and used, based on the assessment result, for example, as that suited for proliferation to a pluripotent stem cell colony or that suited for gene cloning.

Also, the small cell clump may be a single cell. By the cell assessment method of the present invention that further includes a second extraction step of extracting a single cell region within the acquired optical path length image, extraction of just the single cell region is made possible. The cell assessment method may be performed by the cell assessment device of the present invention that further includes a second extraction means extracting a single cell region within the acquired optical path length image.

EFFECTS OF THE INVENTION

According to the present invention, it can be assessed whether or not a cell forming a small cell clump is a stem cell.

BRIEF DESCRIPTION OF DRAWINGS

FIG. 5 shows a graph of optical path lengths (FIG. 5A) and a graph of CN ratios (FIG. 5B) of ES cells that form the small ES cell clump.
FIG. 7 shows a graph of optical path lengths (FIG. 7A) and a graph of CN ratios (FIG. 7B) of differentiated cells that form the small differentiated cell clump.
FIG. 13 shows bright field images (upper row of FIG. 13A), quantitative phase images (lower row of FIG. 13A), a graph of optical path lengths of cell nuclei and cytoplasm (FIG. 13B), and a graph of optical path length ratios (cytoplasm/nucleus) (FIG. 13C) of CHO cells, HeLa cells, OC cells, and hiPS cells.

EMBODIMENTS FOR CARRYING OUT THE INVENTION

The present invention is based on the unexpected finding that even for a stem cell forming a small cell clump "optical path length of the inside of the cell nucleus region<optical path length of the outside of the cell nucleus region" holds regardless of shape and therefore this finding shall be explained first.

Figure 2:
FIG. 2 is a quantitative phase image of the single ES cell.
Figure 3:
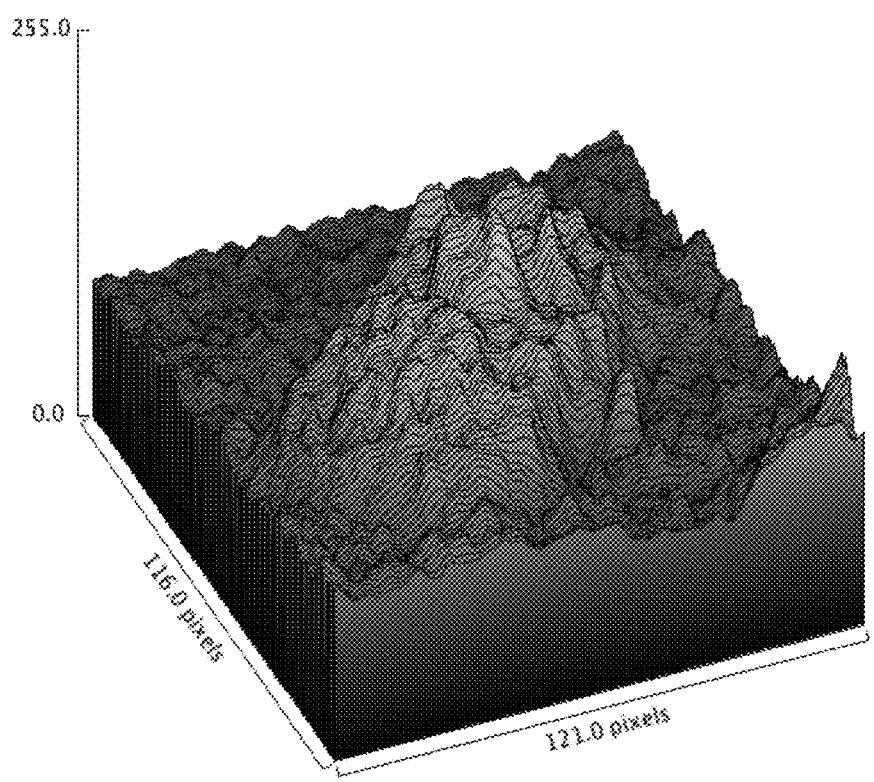
FIG. 3 is a three-dimensional plot image expressing optical path lengths of the single ES cell as brightness.

FIG. 2 is an image (quantitative phase image) acquired by observing a single ES cell with a quantitative phase microscope (and is provided with the symbol W), and FIG. 3 is a three-dimensional plot image expressing optical path lengths of the single ES cell as brightness. Both horizontal axes (X and Y directions) of FIG. 3 express the number of picture elements (pixels) and the vertical axis (Z axis) expresses brightness. A greater numerical value along the vertical axis indicates a greater brightness and a smaller optical path length.

From FIG. 3, it can be understood that "optical path length of the inside of the cell nucleus region<optical path length of the outside of the cell nucleus region" holds even for a single ES cell that does not have a shape like that of a stem cell of a stem cell colony.

Figure 4:
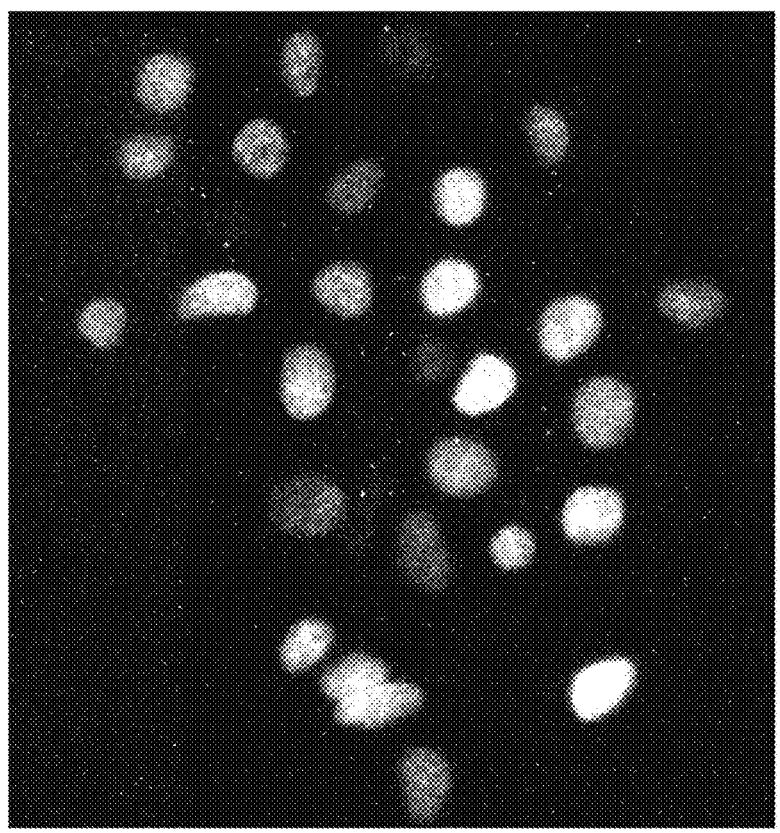
FIG. 4 is an image of a small ES cell clump that has been immunostained by an anti-nanog antibody.
Figure 6:
FIG. 6 is an image of a small differentiated cell clump that has been immunostained by the anti-nanog antibody.

Also, from FIG. 4 and FIG. 5, it can be understood in a small ES cell clump, "optical path length of the inside of the cell nucleus region<optical path length of the outside of the cell nucleus region," that is, "optical path length of the outside of the cell nucleus region/optical path length of the inside of the cell nucleus region" (CN ratio) is greater than 1 and from FIG. 6 and FIG. 7, it can be understood that in a small differentiated cell clump induced from ES cells by retinoic acid (small differentiated cell clump), the CN ratio is less than 1.

FIG. 4 is an image of a small ES cell clump that has been immunostained by an anti-nanog antibody, which is an undifferentiated marker, and bright regions of the image correspond to ES cells that form the small ES cell clump. FIG. 5 shows a graph of optical path lengths (FIG. 5A) and a graph of CN ratios (FIG. 5B) of the cells that form the same small ES cell clump, and from FIG. 5, it is calculated that with the ES cells forming the small ES cell clump, CN ratio=1.06±0.0642 (n=34; the value provided with±is the standard deviation). A comparison of FIG. 4 and FIG. 5 shows that the CN ratios of the cells forming the small ES cell clump are greater than 1.

On the other hand, FIG. 6 is an image of a small cell clump that has been induced from ES cells by retinoic acid and has been immunostained by the anti-nanog antibody, which is an undifferentiated cell marker, and from there being no bright regions in the image, it is confirmed that the small cell clump is a small differentiated cell clump. FIG. 7 shows a graph of optical path lengths (FIG. 7A) and a graph of CN ratios (FIG. 7B) of the cells that form the small differentiated cell clump, and from FIG. 7, it is calculated that with the differentiated cells forming the small differentiated cell clump, CN ratio=0.973±0.122 (n=27; the value provided with±is the standard deviation). A comparison of FIG. 6 and FIG. 7 shows that the CN ratios of the differentiated cells forming the small differentiated cell clump are less than 1.

Preferred embodiments of a cell assessment method, cell assessment device, and cell assessment program of the present invention shall now be described in detail. In the description of the drawings, elements that are the same are provided with the same symbols and redundant description shall be omitted.

(Small Cell Clump)

A "small cell clump" means a cell cluster that includes not more than 200 cells. Although the number of cells may be 1 or may be 2 or more, it is 1 to 100, particularly 1 to 60, and above all 1 to 20. When the number of cells is 1, the small cell clump is a single cell. A small cell clump includes that which cannot proliferate under the presence of an apoptosis inhibitor (for example, the ROCK inhibitor).

The small cell clump may include a stem cell (small stem cell clump) and, in particular, may be constituted only of a stem cell. A single stem cell is a small cell clump, for which the number of stem cells is 1 and which does not include cells besides the stem cell. An example of a cell that is included in a small cell clump and is other than a stem cell is a differentiated cell.

A "stem cell" means a cell having an ability to differentiate into cells of multiple lineages (pluripotency) and an ability to maintain the pluripotency even after undergoing cell division (replication competence). As examples of a stem cell, pluripotent cells, such as an ES cell, iPS cell, mesenchymal stem cell, etc., can be cited, and the stem cell is not restricted to a human stem cell and may be a stem cell of a mouse, monkey, rabbit, dog, cat, etc.

The small cell clump may be a dissociated small clump product obtained from a stem cell colony. As a dissociated small clump product obtained from a stem cell colony, that obtained by dissociating a stem cell colony into small clumps by a physical or chemical means, for example, by pipetting or by treatment by an enzyme, such as trypsin, Accutase, etc., can be cited. With a stem cell, with which adhesion (contact) with other cells has been severed partially or completely in the process of dissociating a stem cell colony into small clumps, the shape of the cell when it formed the stem cell colony is ordinarily not maintained.

Dissociated small clump products obtained from a pluripotent stem cell colony include those capable of proliferating and forming a pluripotent stem cell colony again and those incapable of proliferating and forming a pluripotent stem cell colony again.

Although there is no restriction in regard to a method for acquiring a small cell clump, a method of making a stem cell colony into small cell clumps by dissociation into small clumps can be cited as a method for acquiring a small cell clump, and the dissociation into small clumps may be performed in the process of subculturing the stem cells. As mentioned above, means for dissociation into small clumps include physical and chemical means, for example, pipetting and enzymatic treatment using trypsin, Accutase, etc.

(Measurement Sample)

The small cell clump is then made into a measurement sample S. The measurement sample S is prepared, for example, by injecting a solution, containing the small cell clump, into a slide chamber. A small clump of pluripotent stem cells is ordinarily made to adhere to (contact) the slide chamber.

(Cytometer)

Figure 8:
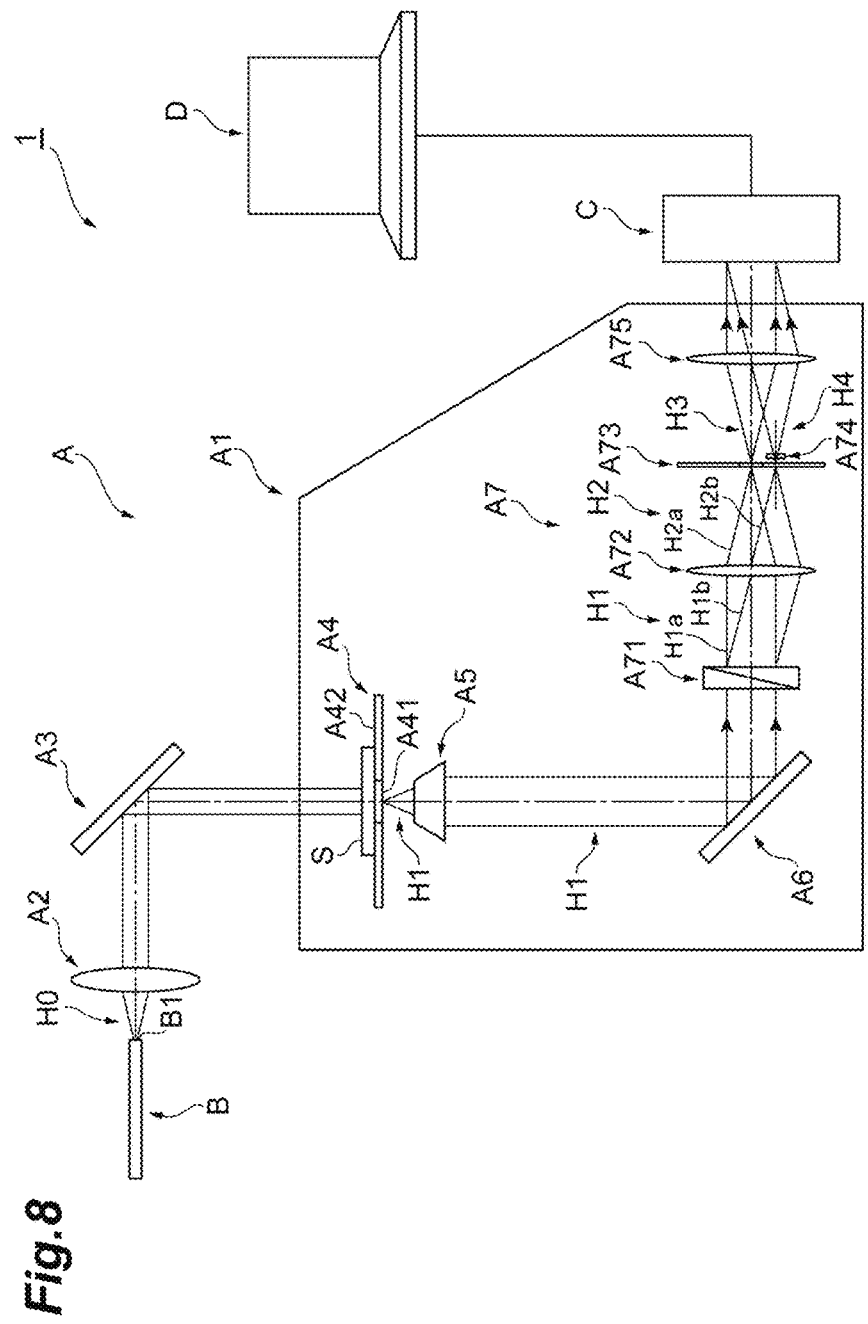
FIG. 8 is an arrangement diagram of a cytometer 1.

The arrangement of a cytometer 1 to be used shall now be described. FIG. 8 is an arrangement diagram of a cytometer 1.

As shown in FIG. 8, the cytometer 1 is mainly arranged from a quantitative phase microscope A and a cell assessment device D.

(Quantitative Phase Microscope)

The quantitative phase microscope A includes, at a light incidence side, a lens A2, facing an emission side end face B1 of an optical fiber B that guides irradiation light H0 (laser light) from an unillustrated light emitting portion, and a reflecting portion A3 reflecting the irradiation light H0 transmitted through the lens A2. On the other hand, an image pickup device C, such as a CCD camera, etc., that captures and obtains an image of an interference fringe (not illustrated; the same applies hereinafter) formed by an optical interference portion A7 is provided at a light emission side of the quantitative phase microscope.

The quantitative phase microscope A includes a microscope main body A1 provided with a sample stage A4 that supports the measurement sample S, an objective lens A5, a reflecting portion A6, and the light interference portion A7.

The sample stage A4 includes, for example, a light transmitting portion A41, which allows transmission of light, at a center, is substantially plate-shaped, and has a placement surface A42 enabling placement of the measurement sample S on an upwardly facing surface. Arrangements are made so that by irradiating light from above in a state where the measurement sample S is placed on the placement surface A42, light (measured light H1) transmitted through the measurement sample S is transmitted through the light transmitting portion A41 and directed toward the objective lens A5. The light transmitting portion A41 may, for example, be that which is formed from glass or other member capable of transmitting light or may simply be a hole. Based, for example, on an operation of an operation portion (not illustrated), the objective lens AS magnifies the incident measured light H1 by a predetermined magnification in accordance with the operation and emits the light as parallel light. The reflecting portion A6 is, for example, a total reflection type mirror and can totally reflect the measured light H1 from the objective lens A5 to introduce it to the light interference portion A7. The light interference portion A7 includes a light splitting element A71, splitting the measured light H1 into two lights H1a and H1b, a condenser lens A72, converting the measured light H1 (H1a, H1b) emitted from the light splitting element A71 into convergent light H2 (H2a, H2b), a spatial filter A73 disposed at a convergence position of the convergent light H2, and a combining lens A75 combining an object light H3 transmitted through the spatial filter A73 and a reference light H4 to form interference fringes. Here, the light splitting element A71 is arranged using a diffraction grating. Further, the light splitting element A71 may be a polarizing light splitting element that splits light into two lights that differ mutually in polarization direction. In this case, the light interference portion A7 includes the light splitting element A71, splitting the measured light H1 into two lights H1a and H1b that differ mutually in polarization direction, the condenser lens A72, performing conversion into convergent light H2 (H2a, H2b), the spatial filter A73 disposed at the convergence position of the convergent light H2, a half-wave plate A74 disposed at an emission side of the object light H3 transmitted through the spatial filter A73, the reference light H4, and the spatial filter A73, and the combining lens A75 combining the object light H3 and the reference light H4, which have been aligned in polarization direction by the half-wave plate A74, to form interference fringes. Or, a polarizer may be disposed in place of the half-wave plate A74 disposed at the emission side of the spatial filter A73 to align the polarization directions of the object light H3 and the reference light H4.

(Cell Assessment Device)

Figure 9:
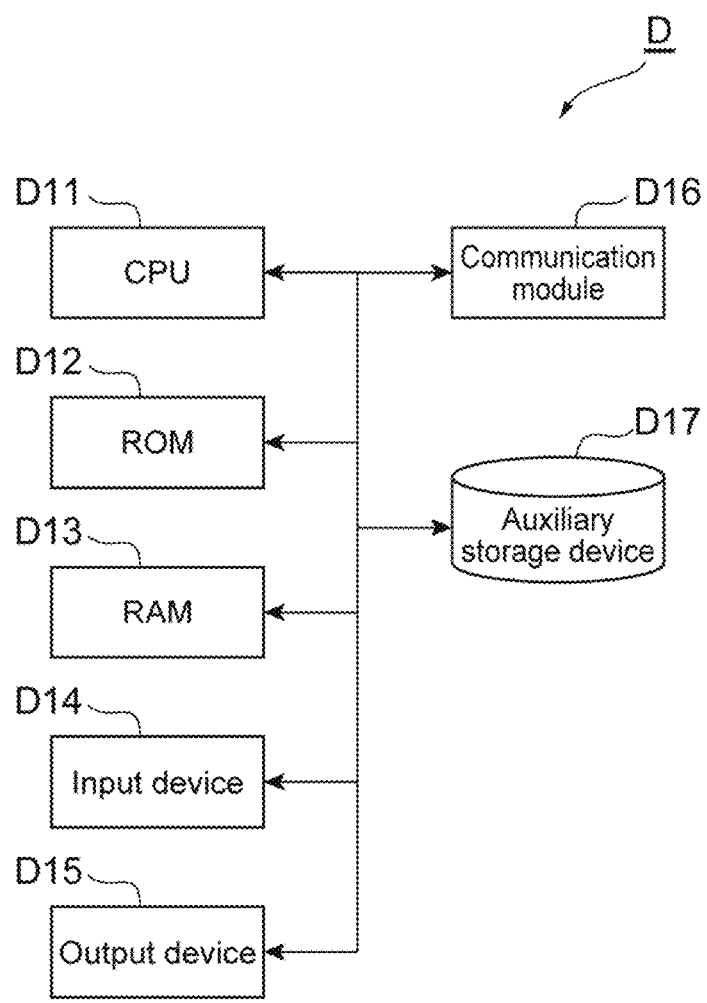
FIG. 9 is a schematic diagram of the hardware arrangement of a cell assessment device D.

The arrangement of the cell assessment device D shall now be described. FIG. 9 is a schematic diagram of the hardware arrangement of the cell assessment device D, and FIG. 10 is a schematic diagram of the functional arrangement of the cell assessment device D.

As shown in FIG. 9, the cell assessment device D is physically arranged as an ordinary computer that includes a CPU D11, main storage devices, such as a ROM D12 and a RAM D13, etc., an input device D14, such as a keyboard and a mouse, etc., an output device D15, such as a display, etc., a communication module D16, such as a network card, etc., arranged to perform sending and receiving of data with another device, for example, the image pickup device C, etc., an auxiliary storage device D17, such as a hard disk, etc. The respective functions of the cell assessment device D to be described below are realized by making predetermined computer software be read into the hardware, such as the CPU D11, the ROM D12, the RAM D13, etc., to make the input device D14, the output device D15, and the communication module D16 operate under the control of the CPU D11 and perform reading and writing of data from and into the main storage devices D12 and D13 and the auxiliary storage device D17.

Figure 10:
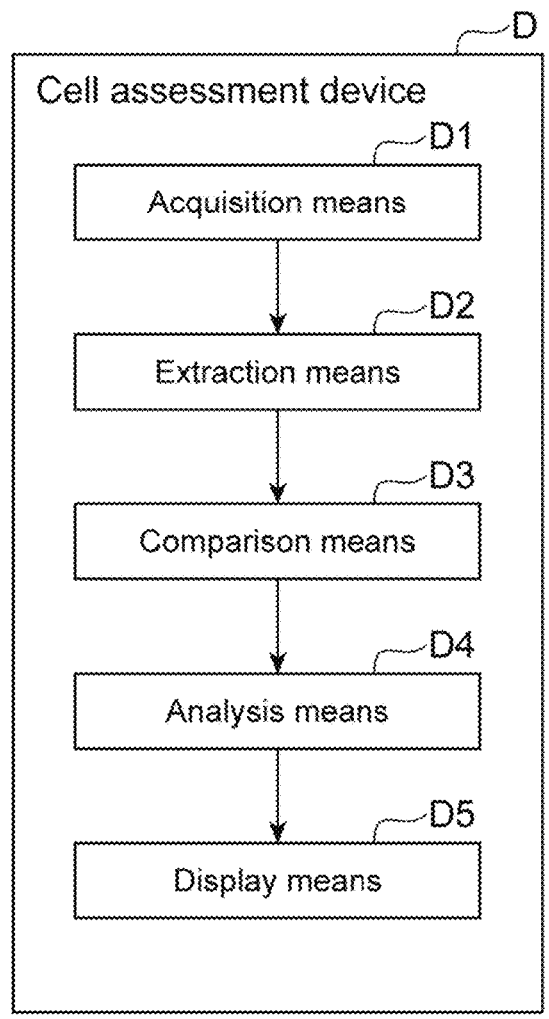
FIG. 10 is a schematic diagram of the functional arrangement of the cell assessment device D.

As shown in FIG. 10, the cell assessment device D includes, as functional components, an acquisition means D1, an extraction means D2, a comparison means D3, an assessment means D4, and a display means D5.

The acquisition means D1 acquires an image (quantitative phase image) from the image pickup device C. The extraction means D2 extracts a cell nucleus region within the acquired quantitative phase image. If a single cell region is to be extracted from within the quantitative phase image, the cell assessment device D further includes a second extraction means (not illustrated) that extracts a single cell region within the acquired quantitative phase image. The comparison means D3 compares an optical path length of an inside and an optical path length of an outside of the extracted cell nucleus region. The assessment means D4 assesses whether or not a cell is a stem cell based on the comparison results. The display means D5 displays the assessment result.

(Cell Assessment Program)

A cell assessment program makes a computer function as the above-mentioned acquisition means D1, the extraction means D2, the comparison means D3, the assessment means D4, and the display means D5. The computer is made to operate as the cell assessment device D by making the computer read the cell assessment program. The cell assessment program is presented, for example, by being stored in a recording medium. As examples of the recording medium, recording media, such as flexible disks, CDs, DVDs, etc., storage media, such as ROMs, etc., semiconductor memories, etc., can be cited.

(Cell Assessment Method)

Figure 11:
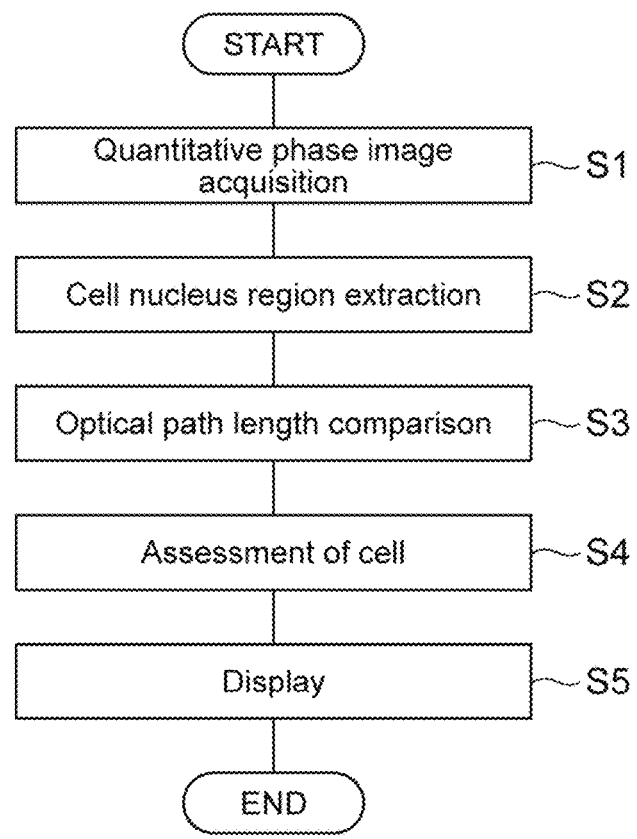
FIG. 11 is a flowchart of a cell assessment method.
Figure 12:
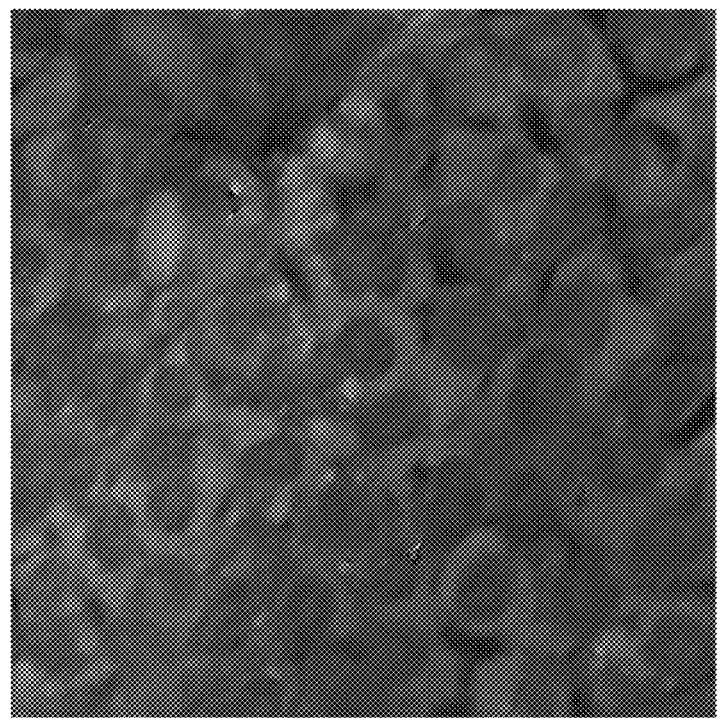
FIG. 12 is a quantitative phase image of stem cells of a stem cell colony.

A cell assessment method performed by the cell assessment device D shall now be described. FIG. 11 is a flowchart of the cell assessment method. By the cell assessment method performed by the cell assessment device D, the assessment of whether or not a cell forming a small cell clump is a stein cell can be made quantitatively and automatically with high precision. Although up until now, whether or not a cell is a stem cell was assessed subjectively by an assessor, it becomes possible to make assessments objectively regardless of the assessor. That is, ambiguous elements, such as the subjectivity and physical condition of an assessor and variation among assessors, can be eliminated and cell assessment based on fixed criteria that is not dependent on the skills of assessors can be performed.

[Acquisition Step S1]

First, the acquisition means D1 acquires the quantitative phase image of the small cell clump from the image pickup device C. Image processing, for example, magnification, reduction, brightness adjustment, or conversion of the quantitative phase image may be performed as necessary.

[Extraction Step S2]

Next, the extraction means D2 extracts a cell nucleus region within the acquired quantitative phase image. Although the extraction means is not restricted in particular, if the brightness of the quantitative phase image is proportional to optical path length, it is also possible to extract the cell nucleus region from the quantitative phase image. Also, a cell nucleus region may be extracted from an image acquired by observation of the same small cell clump by another microscope, for example, a bright field image of the same small cell clump and the corresponding cell nucleus region within the quantitative phase image may be extracted.

If the small cell clump is constituted of two or more cells and images of the two or more cells are included within the quantitative phase image, arrangements may be made to extract the cell nuclear regions of the two or more cells within the quantitative phase image.

If a single cell region is to be extracted from within the quantitative phase image, a second extraction step of extracting a single cell region within the acquired quantitative phase image is further included. The second extraction means calculates an area of an independent cell region present within the quantitative phase image and if the area is less than an area of a single cell region that has been set in advance, the cell region is assessed to be a single cell region and extracted, and oppositely if the area is greater than the area of the single cell region that has been set in advance, the cell region is assessed not to be a single cell region and prevented from being extracted.

Also, if the cytometer 1 includes an interference reflection microscope, just a region of a small cell clump adhered to (contacting) the slide chamber may be extracted.

[Comparison Step S3]

Next, the comparison means D3 compares the optical path length of the inside and the optical path length of the outside of the cell nucleus region extracted in the extraction step S2 and extracts the result. The comparison means D3 may extract the value of "optical path length of the outside of the cell nucleus region/optical path length of the inside of the cell nucleus region" (CN ratio) as the result.

If the small cell clump is constituted of two or more cells and the images of the two or more cells are included within the quantitative phase image, arrangements may be made to extract the comparison results for the two or more cells.

[Assessment Step S4]

Next, the assessment means D4 assesses whether or not the cell is a stem cell based on the comparison result extracted in the comparison step S3. The assessment means D4 assesses the cell to be a stem cell if the comparison result of the comparison step S3 is such that the optical path length of the outside of the cell nucleus region is greater than the optical path length of the inside, that is, if "optical path length of the inside of the cell nucleus<optical path length of the outside of the cell nucleus," and assesses the cell not to be a stem cell if the optical path length of the outside of the cell nucleus region is less than the optical path length of the inside, that is, if "optical path length of the inside of the cell nucleus>optical path length of the outside of the cell nucleus." If the comparison result is the CN ratio, it is assessed that the cell is a stem cell if the CN ratio is greater than 1 and assessed that the cell is not a stem cell if the CN ratio is less than 1.

Also, a degree of differentiation of the cell may be assessed based on the CN ratio. If the value is greater than 1, the degree of differentiation of the cell will also be low, and if the value is less than 1, the degree of differentiation of the cell will also be high.

If the small cell clump is constituted of two or more cells and the images of the two or more cells are included within the quantitative phase image, arrangements may be made to perform the assessment of whether or not a cell is a stem cell for the two or more cells and the proportion of stern cells within the small cell clump may be assessed.

[Display Step S5]

Next, the display means D5 displays the result of assessment in the assessment step S4. For example, whether or not the cell is a stem cell, the value of "optical path length of the outside of the cell nucleus region/optical path length of the inside of the cell nucleus region," the degree of differentiation of the cell, etc., are displayed by the display means D5.

(After the End of Assessment)

After the end of assessment, the small cell clump may be discarded or may be used for another purpose.

Especially in a case where the small cell clump is a dissociated small clump product of a colony of pluripotent stem cells, for example, iPS cells or ES cells, the dissociated small clump product may be selected and used, based on the assessment result, for example, as that suited for proliferation to a pluripotent stem cell colony or that suited for gene cloning.

Although an embodiment in which the optical path length image is a quantitative phase image has been described in detail above, the optical path length image is not restricted to a quantitative phase image. The optical path length image suffices to be an image from which acquisition of optical path length is possible, and the optical path length image may be an image acquired using a phase difference microscope, for example, an image of a phase difference contrast microscope (a phase difference contrast image). In this case, the device is inexpensive and leads to cost savings.

Figure 1:
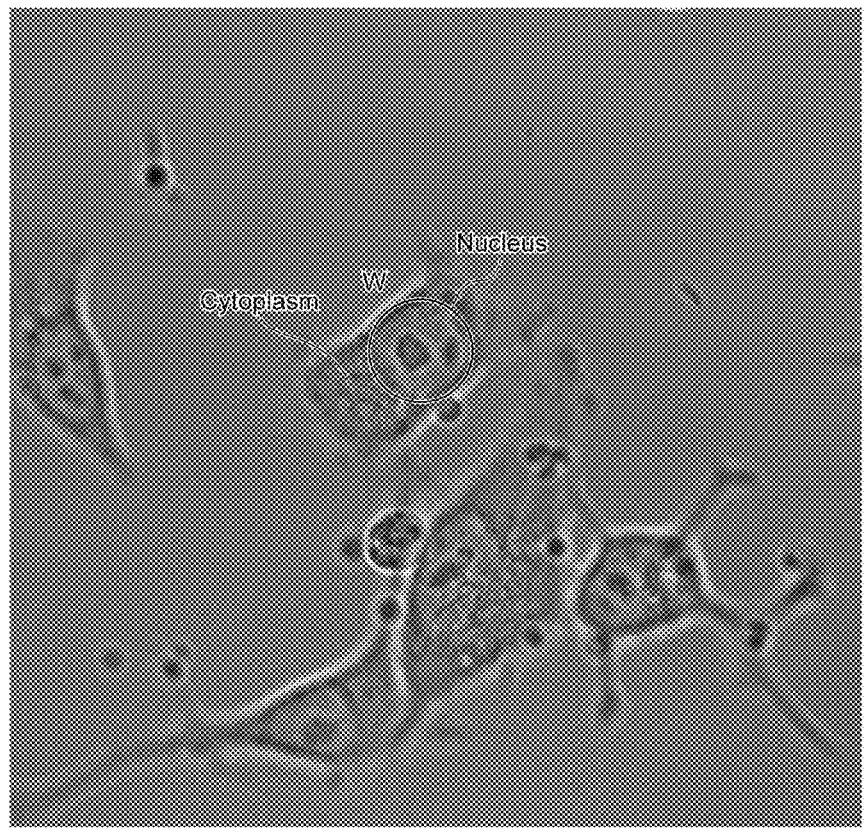
FIG. 1 is a bright field image of a single ES cell.

The single ES cell used to acquire the images of FIG. 1 to FIG. 3 was acquired as follows.

Human ES cells (khES3) were cultured in an mTeSR1 medium (made by STEMCELL Technologies Inc.; registered trademark) using matrigel (made by Becton, Dickinson and Company; registered trademark) as a substrate to form a colony of human ES cells. Thereafter, the cells were peeled off from the substrate and treated with 0.25% trypsin to disperse single human ES cells in the medium. 10 μM of ROCK inhibitor (Y27632: trans-4-[(1R)-1-aminoethyl]-N-4-pyridinylcyclohexanecarboxamide dihydrochloride) were added to the medium. The cells were cultured in the single ES cell state for approximately 3 hours and adhered onto a bottom surface of a dish.

REFERENCE SIGNS LIST

W . . . single ES cell, 1 . . . cytometer, A . . . quantitative phase microscope, A1 . . . microscope main body, B . . . optical fiber, C . . . image pickup device, D . . . cell assessment device, D1 . . . acquisition means, D2 . . . extraction means, D3 . . . comparison means, D4 . . . assessment means, D5 . . . display means.

The invention claimed is:

1. A cell assessment method, comprising:
acquiring an optical path length image of a small cell clump adhered to a slide chamber,
extracting a cell nucleus region within the acquired optical path length image,
comparing an optical path length of an inside of the extracted cell nucleus region and an optical path length of an outside of the extracted cell nucleus region, and
assessing whether or not a cell is a stem cell based on the comparison results.

2. The cell assessment method according to claim 1, wherein the small cell clump is a dissociated small clump product of a pluripotent stem cell colony.

3. The cell assessment method according to claim 2, wherein the pluripotent stem cell is an iPS cell or an ES cell.

4. The cell assessment method according to claim 1, wherein the small cell clump is a single cell.

5. The cell assessment method according to claim 4, further comprising extracting a single cell region within the acquired optical path image.

6. A cell assessment device, comprising:
a non-transitory memory storing information about an optical path length of an image; and
one or more hardware processors coupled to the non-transitory memory and configured to read instructions from the non-transitory memory to cause the device to perform operations comprising:
acquiring an optical path length image of a small cell clump adhered to a slide chamber,
extracting a cell nucleus region within the acquired optical path length image,
comparing an optical path length of an inside of the extracted cell nucleus region and an optical path length of an outside of the extracted cell nucleus region, and
assessing whether or not a cell is a stem cell based on the comparison results.

7. The cell assessment device according to claim 6, the device further configured to extract a single cell region within the acquired optical path length image.

8. A cell assessment program stored on a non-transitory computer-readable medium arranged to make a computer function as
an acquisition means acquiring an optical path length image of a small cell clump adhered to a slide chamber,
an extraction means extracting a cell nucleus region within the acquired optical path length image,
a comparison means comparing an optical path length of an inside of the extracted cell nucleus region and an optical path length of an outside of the extracted cell nucleus region, and
an assessment means assessing whether or not a cell is a stem cell based on the comparison results.

9. The program according to claim 8, further arranged to make the computer function as
a second extraction means extracting a single cell region within the acquired optical path length image.

* * * * *